(12) United States Patent
Abrahmsohn

(10) Patent No.: US 11,116,789 B2
(45) Date of Patent: *Sep. 14, 2021

(54) COMPOSITIONS AND METHODS FOR PAIN RELIEF WITHOUT NUMBNESS

(71) Applicant: Glenn Abrahmsohn, Key Biscayne, FL (US)

(72) Inventor: Glenn Abrahmsohn, Key Biscayne, FL (US)

(*) Notice: Subject to any disclaimer, the term of this patent is extended or adjusted under 35 U.S.C. 154(b) by 305 days.

This patent is subject to a terminal disclaimer.

(21) Appl. No.: 14/825,761

(22) Filed: Aug. 13, 2015

(65) Prior Publication Data

US 2015/0342986 A1 Dec. 3, 2015

Related U.S. Application Data

(63) Continuation of application No. PCT/US2014/016939, filed on Feb. 18, 2014.

(60) Provisional application No. 61/800,415, filed on Mar. 15, 2013, provisional application No. 61/765,847, filed on Feb. 18, 2013.

(51) Int. Cl.
| | |
|---|---|
| *A61K 33/00* | (2006.01) |
| *A61K 33/14* | (2006.01) |
| *A61K 31/167* | (2006.01) |
| *A61K 33/06* | (2006.01) |
| *A61K 45/06* | (2006.01) |
| *A61K 31/137* | (2006.01) |
| *A61K 9/00* | (2006.01) |

(52) U.S. Cl.
CPC ............ *A61K 33/00* (2013.01); *A61K 9/0014* (2013.01); *A61K 9/0019* (2013.01); *A61K 31/137* (2013.01); *A61K 31/167* (2013.01); *A61K 33/06* (2013.01); *A61K 33/14* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,192,527 | A | * 3/1993 | Abrahmsohn | ......... A61K 31/19 424/678 |
| 2010/0124575 | A1 | * 5/2010 | Abrahmsohn | ....... A61K 31/167 424/717 |

OTHER PUBLICATIONS

Hung et al., Regional Anesthesia and Pain Medicine, 34: 333-339 (2009).*
Vesikari et al., Pediatr Infect Dis J., 29: 314-318 (2010).*
United States Pharmacopeial Convention, USP 34, pp. 1-14 (2010) downloaded from http://www.usp.org/sites/default/files/usp_pdf/EN/USPNF/USP34-NF29General%20Notices.pdf Aug. 17, 2016.*

* cited by examiner

*Primary Examiner* — Melissa L Fisher
(74) *Attorney, Agent, or Firm* — Ted Whitlock; Registered Patent Attorney, PA

(57) ABSTRACT

Methods for providing post-operative pain control or relief, without a medically significant degree of numbness, to a patient are disclosed. Methods include, for example, administering bicarbonate and a calcium salt to an area of a patient during a surgical or dental procedure, near completion of a surgical or dental procedure or immediately following a surgical or dental procedure, in an area previously administered or containing a regional or local anesthetic, in an amount sufficient to provide the patient with pain control or relief, without a medically significant degree of numbness, for a period of time after the surgical or dental procedure.

14 Claims, No Drawings

COMPOSITIONS AND METHODS FOR PAIN RELIEF WITHOUT NUMBNESS

CROSS-REFERENCE TO RELATED APPLICATIONS

This application claims priority to International Patent Application, PCT/US2014/016939, filed Feb. 18, 2014, which claims the benefit of U.S. Provisional Patent Application Ser. No. 61/800,415, filed Mar. 15, 2013, and U.S. Provisional Patent Application Ser. No. 61/765,847, filed Feb. 18, 2013.

BACKGROUND

Anesthetic agents are pharmacologically active agents that block nerve conduction when applied in therapeutically effective amounts, resulting in a lack of sensation in the affected part of the body, including the lack of temperature, touch, and/or pain sensations. Anesthetics may be applied by injection, or in the form of ointments, jellies, pastes, topical solutions, suspensions, or other forms.

As recognized in the medical and pharmaceutical arts, anesthetics are typically divided into the categories of "general" and "local" anesthetics, where the "local" anesthetics may be further subdivided into "local" and "regional" anesthetics. For purposes of this invention, the term "anesthetic" or "local anesthetic" refers to a local or regional anesthetic, as distinguished from a "general" anesthetic.

Anesthetics have formed one of the key components in the advancement of medicine and dentistry. Many medical and dental procedures would be impossible or very uncomfortable for patients if anesthetics were not available as a numbing agent, significantly reducing, if not eliminating, pain resulting from invasive medical procedures. Injury or disease can also cause extended or chronic pain wherein administration of anesthetics may also be useful.

As conventionally understood, an anesthetic agent may inhibit pain by blocking the nerve or nerve impulse; accordingly, the patient feels no "pain," but also experiences a numbing effect, having no other sensations, such as touch or temperature sensation, at that site or region of administration. Therefore, local or regional anesthetic agents in conventional use provide concomitant inhibition of temperature, touch, pressure, and pain, as well as other sensations due to the blocking of the nerve impulse. However, inhibition of pain by blocking the nerve impulse is not an analgesic effect, per se; rather, it is inhibition of sensation normally transmitted by the nerve impulse.

The inhibition of sensation by the blocking of the nerve, and the loss of sensation or sensory response to a stimulus, such as high or low temperature, touch, pressure, pain, or the like, which is normally associated with the blocking of the nerve impulses, can be considered the "anesthetic effect," referred to herein as "numbness" or "numbing effect." Thus, "numbness or numbing effect" refers to a loss of sensory perception or sensation in an area or region of a body administered an anesthetic agent, or an area or region of the body served by a nerve which is the target of an administered anesthetic agent.

While the use of anesthetics is vital, undesired medical issues or side effects can also be created by anesthetics. Overdoses of anesthetics can cause many undesirable effects, including tissue damage and even death. The application of anesthetics may cause some degree of pain. Even the numbness or substantial loss of sensory perception, such as touch, temperature or pain sensation that accompanies the use of most anesthetics can have serious consequences. Humans or animals administered an anesthetic may suffer further injury because they are unaware of damage to an anesthetized site that has become numb.

Attempts have been made to prevent or alleviate the undesirable effects that may accompany the use of anesthetics. For example, U.S. Pat. No. 5,192,527 describes a method for alleviating one of the other undesirable effects of anesthesia, i.e., the extended numbness that accompanies the use of certain anesthetics. As described in the '527 patent, administration of a reversing agent, which includes, among others, a solution containing bicarbonate ($NaHCO_3$) injected into a site previously treated with an anesthetic, can reverse all physiological effects of the anesthetic. The '527 patent, however, does not describe or recognize reversal of selected physiological effects of the anesthetic, e.g., reversing "numbness" caused by the anesthetic, but without reversal of pain inhibition.

U.S. Pat. No. 5,209,724 also describes the use of bicarbonate in combination with an anesthetic, and the optional use of $CO_2$. However, the bicarbonate is used in low concentrations to upwardly adjust the pH of common dental anesthetics, thereby reducing or eliminating the "bee sting" pain that often accompanies the injection of low pH dental anesthetics.

The amounts of bicarbonate used in comparison to the amount of anesthetic used are intentionally low (on the order of 1:10 ratio of bicarbonate:anesthetic) in accordance with known precautions to prevent precipitation and/or crystallization of the anesthetic or the bicarbonate from solution. The '724 patent does not describe any reversal of any aspect of anesthetic effect, and in fact describes the bicarbonate as providing an early onset of effective anesthesia and the possible enhancement of the duration and effect of the anesthetic.

In addition, controlled release formulations have been described for sustained effect of beneficial agents, including anesthetic agents. For example, a sustained-release injectable formulation is described in U.S. Pat. No. 5,385,738, which comprises a suspension of a powder comprising an active ingredient and a pharmaceutically acceptable biodegradable carrier (e.g. proteins, polysaccharides and synthetic high molecular compounds, preferably collagen, atelocollagen, gelatin, and a mixture thereof) in a viscous solvent (e.g. vegetable oils, polyethylene glycol, propylene glycol, silicone oil, and medium-chain fatty acid triglycerides).

Long-term local anesthesia is also described in U.S. Pat. No. 6,926,905, which provides a liposomal anesthetic formulation prepared by a dehydration-rehydration method. In this method, lyophilized liposomes encapsulating the local anesthetic are rehydrated by agitating them in an aqueous medium, and optionally washing the rehydrated liposomes in hyperosmotic saline solution. Substituted ammonium and polyanions are described as being useful for loading and retaining entities inside liposomes, as described in U.S. Pat. No. 8,147,867.

U.S. Pat. No. 6,921,541 describes a formulation and method for inducing sustained regional local anesthesia in a patient comprising a substrate comprising a local anesthetic and an effective amount of a biocompatible, biodegradable, controlled release material prolonging the release of the local anesthetic from the substrate to obtain a reversible local anesthesia when implanted or injected in a patient, and a pharmaceutically acceptable, i.e., non-toxic, non-glucocorticoid augmenting agent effective to prolong the duration of the local anesthesia for a time period longer than that obtainable from the substrate without the augmenting agent.

A method and ophthalmic preparation suitable for sustained and extended corneal analgesia and for repeated administration consisting of a sub-anesthetic (0.4%) concentration of lidocaine, are described in U.S. Pat. No. 6,350,781.

A method and an injectable depot gel composition for systemic and local delivery of a beneficial agent to a subject, providing controlled release of the beneficial agent over a period equal to or less than two weeks after administration, preferably a period of about 3 to about 7 days, is described in U.S. Pat. No. 8,278,330.

The above patents are hereby incorporated by reference in their entirety.

Despite the various advances that have been made to alleviate the undesirable effects of anesthetics, many problems still remain. In particular, there is a need for a method for providing anesthesia of medically useful duration that partially or fully alleviates pain while reversing or not creating a medically significant degree of numbness.

SUMMARY

Embodiments disclosed herein provide a composition and method which provides or extends the control or relief of pain (chronic or acute) in a patient administered a local anesthetic agent, but without continued numbing effect typically associated with administration of the local anesthetic agent. A kit or article of manufacture comprising one or more compositions, devices and, optionally, written instructions, for using a composition of the invention or for carrying out a method of the invention, are also part of this invention.

In some aspects embodiments include providing anesthetic analgesia or analgesic effect (control or relief of pain) without any medically significant degree of numbness. For convenience of reference herein, the term Local Anesthetic Analgesia Without Numbness, or "LAAWON," is coined and used herein to describe and refer to this novel effect.

In summary, embodiments disclosed herein include methods for providing in a patient, local or regional analgesia without a medically significant degree of numbness, wherein the area is also administered, previously or concomitantly, or contains, a local or regional anesthetic agent, wherein the method comprises administering to the patient, in the area administered or containing the local or regional anesthetic, an effective amount of a composition comprising about 1% to about 15% of a bicarbonate, nitrate, or phosphate salt in aqueous solution, and an amount greater than zero but less than about 1.2 milligrams/100 milliliter of a pharmaceutically acceptable calcium salt, such as calcium chloride.

Compared to a composition comprising a conventional buffer, or salt, such as sodium bicarbonate, alone, used to reverse substantially all anesthetic and analgesic effect, a composition as disclosed herein, comprising a combination of a buffer (such as sodium bicarbonate) and about 1.0 to about 1.2 milligrams/100 ml of a calcium salt, such as calcium chloride, not only can provide analgesia without numbness (LAAWON), but certain embodiments can unexpectedly extend the duration of the LAAWON effect, and certain embodiments can further unexpectedly reduce the time between administration of the composition and the onset of the LAAWON effect.

Advantageously, the methods disclosed herein can be effective without administration of an additional opiate, NSAID, amide or amine analgesic, although the administration of additional or other analgesics can be used in conjunction with the invention.

A composition in accordance with the invention may comprise about 4% to about 6% sodium bicarbonate, and in some embodiments about 4.8% sodium bicarbonate, plus 0.1 mM (about 1.11 mg/100 ml) of calcium salt, such as calcium chloride. This and other compositions according to embodiments disclosed herein may have a pH of greater than about 7.0, or in some embodiments from about 7.0 to about 11.0, and in other embodiments from about 7.6 to about 8.6.

In use, the volume of the composition administered can be up to about 1-15 ml, as typical for regional blocks used in non-dental procedures, and may be from about 2 to about 4 mls for use in dental procedures.

The method can include administering a regional or local anesthetic agent to the patient prior to administration of the compositions disclosed herein.

The method can include administering the regional or local anesthetic, as well as compositions disclosed herein, topically, intradermally, intramuscularly, intravenously, subcutaneously, epidurally, by infusion, or by injection.

In some embodiments, the method comprises administering the composition and regional or local anesthetic agent at a ratio of at least 0.4:1, and in some embodiments at a ratio of about 1:1, 2:1, 3:1, 4:1, 5:1, 6:1, 7:1, 8:1, 9:1, 10:1, or greater.

The methods disclosed herein can be used with commonly administered anesthetic agents, including editocaine, hexylcaine, iontocaine, decicaine, dibucaine, dyclonine, pramoxine, proparacaine, oxybuprocaine (Benoxinate), bupivicaine (MARCAINE), levobupivicaine, lidocaine, a lidocaine derivative, mepivacaine, prilocaine, ropivicaine, articaine (SEPTOCAINE), trimecaine, fentanyl, morphine, benzocaine, chloroprocaine, cocaine, tetracain (PONTOCAINE) and procaine (Novocaine). Methods disclosed herein can advantageously be used before, during, or following a surgical or dental procedure such as, but not limited to: cancer or tumor surgery, trauma surgery, cosmetic surgery, abdominal surgery, head or neck surgery, orthopedic surgery, back or spine surgery, arthroscopic surgery, brain surgery, ear, nose or throat surgery, eye surgery, amputation, liposuction, rhinoplasty, graft or transplant surgery, a biopsy, skin surgery, breast surgery, prosthetic surgery, fetal surgery, gastroenterologic surgery, thoracic surgery, bladder surgery, heart surgery, liver surgery, pancreas surgery, kidney surgery, lung surgery, gallstone surgery, hernia surgery, shoulder, arm, leg, pelvis, hip, knee, elbow or ankle surgery, uterine or vaginal surgery, routine child birth, cesarean section procedure or episiotomy, blood vessel surgery, prostate surgery, colon or rectal surgery, laser surgery, oral surgery, periodontal surgery, dental implant or tooth repair or extraction.

A kit for providing in a patient, local or regional analgesia without a medically significant degree of numbness, in accordance with various embodiments can include two or more of the following: an anesthetic agent, a composition for reversing numbness but not pain according to the subject invention, written instructions for using the reversing composition, a device for determining pH of the composition, one or more syringes, one or more syringe needles, provided separately, and housed together in a single packaging unit. The pH determining device can be integral with the packaging, and the written instructions can be provided on paper or in electronic storage format.

DETAILED DESCRIPTION

Embodiments disclosed herein relate to and include compositions and methods for providing or extending the control or relief of pain (analgesia) effect of a regional and local anesthetic agent, but without the continued effect of a medically significant degree of numbness (anesthesia) normally associated with the local or regional anesthetic agent. This Local Anesthesic Analgesia Without Numbness, is referred to herein as the acronym, LAAWON.

Without being held or limited to any particular activity of the selective reversal method, the subject method is believed to result from the buffer composition converting, in situ, the regional or local anesthetic agent into a slow or prolonged release regional or local anesthetic. The administration of the buffer composition is believed to create a depot of local anesthetic agent at the site or area of administration thereof, thereby providing slow or sustained release of the local anesthetic agent which inhibits pain, but does not continue nerve blockage to the extent where touch or temperature sensation (numbness) is inhibited to a medically significant degree.

A "regional" or "local" anesthetic means an anesthetic agent having an effect limited to a given area or a part of the body of a patient that remains conscious, as opposed to a general anesthesia where a subject loses consciousness— although a patient may be sedated to relax the patient. A regional anesthetic affects a large part of the body. A local anesthetic affects a smaller or more specific area or part of the body.

Regional anesthesia generally involves the administration of anesthetics to block the nerve function to a specific part of the body, such as a limb (e.g., leg, arm, lower part of the body, etc.), so a patient does not feel pain in that specific part of the body, but retains sensation in other parts of the body. Specific non-limiting examples of regional anesthetics include epidural anesthesia, spinal anesthesia, brachial plexus blocks, and intravenous regional techniques (e.g., Bier blocks). Regional anesthesia further includes nerve blocks that affect major peripheral nerves such as femoral and sciatic nerves.

Local anesthesia generally involves administration of anesthesia to block peripheral nerves at the region or area in which is it desired to suppress pain. A local anesthetic is typically administered by injection or applied to a body surface (e.g., topically via a liquid, paste, ointment, jelly or cream), and then diffuses into nerves where it inhibits the propagation of one or more of pain, muscle contraction, regulation of blood circulation and other body functions. Relatively high doses or concentrations of anesthesia inhibit all sensation (pain, touch, temperature, etc.) as well as muscle control. Lower doses or concentrations of slow release anesthetic agents, such as lidocaine, can inhibit pain sensation while minimizing the effect on muscle control.

Anesthesia administered regionally or locally therefore includes, among others, surface anesthesia, infiltration, field block anesthesia, nerve block anesthesia, intravenous regional anesthesia, spinal anesthesia and epidural anesthesia.

Surface anesthesia involves topical administration to the skin or mucous membranes such as those found in the nose, mouth, throat, tracheo-bronchial tree, esophagus and the genitourinary tract.

Infiltration anesthesia typically is an injection of anesthetic directly into the desired tissue. This anesthesia can be superficial so as to include only the skin or include deeper structures including intra-abdominal organs. Infiltration or other anesthetic techniques permit effective anesthesia delivery without disruption of normal body functions.

Field block regional anesthesia typically is a subcutaneous injection of local anesthetic to interrupt nerve transmission proximal to the site to be anesthetized.

Nerve block regional anesthesia typically involves injection of anesthetic into or about individual or peripheral nerves or nerve plexus thereby affecting larger areas.

Intravenous regional anesthesia typically involves injection into a vein of an extremity previously exsanguinated and kept exsanguinated.

Spinal anesthesia typically involves injection of anesthetic into the lumbar subarachnoid space.

Epidural anesthesia typically involves injection of anesthetic into the epidural space.

Anesthetic agents include esters or amides of benzylic acid derivatives, such as benzocaine, chloroprocaine, cocaine, tetracain (PONTOCAINE) and procaine (Novocaine). Anesthetics include prodrugs. Regional and local anesthetics useful in practicing the methods of the invention include a large number of compounds. Specific non-limiting examples of regional and local anesthetics include editocaine, hexylcaine, iontocaine, decicaine, dibucaine, dyclonine, pramoxine, proparacaine and oxybuprocaine (Benoxinate). Anesthetics include amino amides and opiates/opioids. Specific non-limiting examples of amino amide anesthetics include bupivicaine (MARCAINE), levobupivicaine, lidocaine, lidocaine derivatives (e.g., N-(2,6-Dimethylphenylcarbamoylmethyl)triethylammonium bromide, also referred to as QX-314, a quaternary derivative of lidocaine, 2-(trimethylamino)-N-(2,6-dimethylphenyl)acetamide also referred to as QX-222, and N-beta-phenylethyl lidocaine quaternary ammonium bromide), mepivacaine, prilocaine, ropivicaine, articaine (Septocain.)

Anesthetic agents can be in a hydrochloride acid-addition salt. Typically, regional or local anesthetics are administered in a solution (e.g., aqueous solution), for example, a form of hydrochloride acid-addition salt in an aqueous solution.

Doses can be based upon current existing treatment protocols, empirically determined, determined using animal disease models or in human clinical studies. For example, a regional or local anesthetic is typically administered in a solution from about 0.5 to 5% and in other mixtures of up to 20% or 30% or more by weight/volume. The amount administered depends on the route or area for administration. For application to an oral cavity (e.g., mouth or buccal tissue), the amount administered generally is no more than 6 ml of a 2% solution.

Typical amounts of lidocaine that are commercially available as the hydrochloride salt, are used in preparations comprising about 0.5 to about 20% by weight, volume (up to about 7 mg/kg body weight), some with and some without epinephrine for infiltration, about 1 to 4% for block and about 5% for topical mucosal anesthesia. Bupivicaine is used commercially as a hydrochloride in solutions from about 0.25 to about 0.75%; chloroprocaine, typically as the hydrochloride in solutions of about 1 to 3%. Ediocaine is typically used as a hydrochloride in solutions of about 1 to 2%. Mepivicaine is typically used in solutions of from about 1 to 3%, optionally with or without levonordenphedrine as a vasoconstrictor. Prilocaine is typically used as the hydrochloride in solution at about 4%, optionally with or without epinephrine as a vasoconstrictor. Procaine is typically used as the hydrochloride in solutions of about 0.25 to 0.5% for infiltration, 0.5% to 2% for peripheral nerve block and 10% for spinal anesthesia. Tetracaine is typically used in solutions as the hydrochloride of about 5% as an ointment and about 2% for application to the mucous membranes or throat. Tetracaine for injection is available in solutions or ampules containing the dry salt, as well as ointments of 5% and creams of 1%.

Table 1, below, shows typical types, concentrations, and amounts of local or regional anesthetics used in commonly performed medical or dental procedures, and volumes of the subject composition used in conjunction with such procedures. The types, concentrations, and amounts in Table 1 are exemplary only, and are not intended to be limiting.

TABLE 1

CONCENTRATION OF AMIDE LOCAL ANESTHESIA

| SITE OF OPERATION | 1.5% LIDOCAINE or EQUIVALENT | 0.5% MARCAINE/ 0.5% BUPIVICAINE | PAIN CONTROL for creation of LAAWON Volume of Buffered Composite Solution |
|---|---|---|---|
| Upper abdominal | 30 ml | 30 ml | 30-90 ml |
| Lower abdominal | 20 ml | 20 ml | 20-60 ml |
| Hernias & varicose veins | 20 ml | 20 ml | 20-60 ml |
| Perineal/bladder-neck Operations | 15 ml | 15 ml | 15-45 ml |
| {Cervical plexus blocks | 1% Lido 10-20 ml | 10-20 ml | 10-60 ml} |
| {2nd block-cervical plexus | 1.0-1.5% Lido 5 ml | 5 ml | 5-15 ml} |
| {3rd & 4th cervical vertebrae | | | |
| Intercostal block | 0.5-1% Lido 3-4 ml | 3-4 ml | 3-9 ml |
| Para verterbral somatic n.block | 1% Lido 5 ml | 5 ml | 5-15 ml |
| Brachial plexus | 1.2% 5-10 ml @ ea Site total of 30-40 ml | 5-10 ml @ ea. site total of 30-40 ml | 5-15 ml max @ 90-120 ml |
| Interscalene brachial Plexus block | 1-1.5% Lido 20-40 ml | 20-40 ml | 20-120 ml |
| Superclavicular block Nerve block @ elbow | 1-1.5% 20-25 ml | 20-25 ml | 20-75 ml |
| Median nerve | 2% Lido 2-3 m. | 2-3 ml | 2-9 ml |
| Radial nerve | 2% Lido 10 ml | 10 ml | 10-30 ml |
| Ulnar nerve Nerve block @ wrist | 2% Lido 2 ml | 2 ml | 2-6 ml |
| Medial nerve | 2% Lido 1-2 ml | 1-2 ml | 1-6 ml |
| Ulnar nerve | 2% Lido 2 ml | 2 ml | 2-6 ml |
| Radial nerve | 2% Lido 2 ml | 2 ml | 2-6 ml |
| Hand & Digital blocks | avoid excessive distention 1% 5 ml | 5 ml | & no epi 5 ml |
| Femoral nerve block | 1% Lido | 5-10 ml | 5-30 ml |
| Lateral Femoral cutaneous Nerve block | 1% Lido 5-10 ml | 5-10 ml | 5-30 ml |
| Sciatic nerve block | 2% Lido 10-20 ml | 10-20 ml | 10-60 ml |
| Intravenous regional Anesthesia | | | =to 3xvolume |
| Epidural anesthesia | 1.5% 10 ml | 0.5% 10 ml | 10-30 ml |
| Continuous epidural Anesthesia | 0.2% Bupivicaine @ rate of 2 ml/hr for 48 hours | 2 ml/hr | 2 ml/hr |
| Spinal anesthesia | 0.5% Amethocaine in 10% Glucose over 20 secs. | 2 ml | 2 ml-plus if needed |

In accordance with the method disclosed herein, during or after a regional or local anesthesia has been administered to the patient, a composition of the invention can be administered to the patient whereby the numbing effect of the anesthetic agent is reversed, but the control or relief of pain (analgesic) effect is not reversed, thus providing Local Anesthetic Analgesia Without Numbness (LAAWON).

A "medically significant degree of numbness or numbing effect" is a loss of sensation, including touch, temperature, or other sensation, which could impair reactions to potentially harmful external stimuli. For example, a medically significant degree of numbness or numbing effect can cause a person to fail to remove a hand from a hot surface, or can cause damage to the mouth or tongue while chewing due to lack of touch or kinesthetic sensation following administration of an anesthetic.

Thus, as used herein, the terms "numbing," "numbness," "numbing effect," whether or not qualified by the term, "medically significant," may be used interchangeably and mean a subjective loss of sensation which a person would describe as feeling "numb" (or without normal sensory perception) as compared to the same sensation or feeling if not administered an anesthetic agent. For purposes of embodiments disclosed herein, this numbness or numbing effect is distinguished from the sensation of pain experienced or felt by a person.

"Reversal" of the anesthetic using an anesthetic reversing agent is described in the prior art and is generally understood to reverse the numbing effect and to return all sensation to the patient, i.e., returning temperature, touch, and pain sensation. However, in accordance with embodiments disclosed herein, it has been discovered that selective reversal of the numbing effect (reversal of inhibition of touch and temperature sensation), without reversal of the inhibition of pain sensation can be achieved by administering a buffer composition to the area previously administered a local or regional anesthetic agent. Thus, the continued or extended inhibition of pain sensation provides pain relief, here termed "anesthetic analgesia" because it is analgesia from the anesthetic, but without any medically significant degree of numbness.

Thus, embodiments disclosed herein maintain control or relief of pain in an area of the body, while reversing the numbness or numbing effect typically associated with administration of anesthetic. A composition or method, as disclosed herein, can reverse or significantly reduce numbness or numbing effect of an anesthetic, without reversing or significantly reducing the relief or control of pain. Said another way, the compositions and methods disclosed herein can reverse or significantly reduce the numbing, or "anesthetic," effect, without reversing or significantly reducing the pain-relief, or "analgesic," effect associated with an anesthetic agent.

Embodiments disclosed herein concern the unexpected discovery that the use or administration of a solution comprising an inorganic salt or organic buffer, e.g., sodium bicarbonate, calcium chloride, TRIS buffer, or the like, in certain ratios to the amount of local anesthetic, can result in continued or extended analgesia or analgesic effect (pain relief or pain control) without the inhibition of numbing or numbing effect (loss of temperature, touch, and other sensation) typically associated with local anesthetic administration.

Embodiments disclosed herein provide compositions and methods for continued or extended relief or control of pain (chronic or acute) to a patient without any medically significant degree of numbness, which would typically be expected by administration of the anesthetic agent. Embodiments disclosed herein include providing pain relief or pain control using a local anesthetic substance that is used to numb an area of the body, but without continued (i.e., reversed) numbing effect.

In addition, it is a further advantage of various embodiments that the composition comprising about 4.8% sodium bicarbonate plus about 1.11 mg/100 ml a pharmaceutically acceptable calcium salt, such as calcium chloride, can decrease the time for onset of reversal of the numbing effect. Pharmaceutically acceptable calcium salts include but are not limited to calcium acetate, calcium chloride, calcium gluconate, calcium phosphate, or calcium sulfate. Decreasing the time of onset of reversal of the numbing effect can prevent injury and generally allow the subject being treated to otherwise function normally as quickly as possible.

Embodiments disclosed herein further include providing pain control or relief without any medically significant degree of numbness arising from the local or regional anesthetic, wherein, advantageously, analgesia is provided without the use of another potentially harmful analgesic, such as an opioids or NSAID. Nevertheless, additional pain relievers or pain medication, such as NSAIDs or opioids, can be used in combination with the invention.

Compositions, in accordance with some embodiments, may comprise a bicarbonate, phosphate, nitrate, or TRIS buffer solution, wherein the solution further comprises calcium chloride ($CaCl_2$). In some embodiments, compositions disclosed herein comprise about 0.10 mg/100 ml to about 1.5 mg/100 ml $CaCl_2$ in about 1% to about 10% sodium bicarbonate (aqueous) solution.

In one embodiment, a composition of the invention can comprise an aqueous solution comprising about 4.8% sodium bicarbonate and about 1.11 mg/100 ml calcium chloride. In another embodiment, the composition has a pH of about 7.6 to about 8.6 (more preferably, the pH is slightly higher than 8.6, or about 8.61). In some embodiments, absent a suitable alternative pharmaceutically acceptable solvent vehicle, $CaCl_2$ may be used at no more than about 1.2 mg/100 ml, and preferably about 1.10 to about 1.11 mg/100 ml because there is an upper limit to the amount of $CaCl_2$ that can be present in an aqueous sodium bicarbonate solution, as described herein, before a precipitate is formed from the solution. The precipitate can be $CaCl_2$, the sodium bicarbonate, the anesthetic agent, or calcium carbonate formed by the reaction of $CaCl_2$ with the sodium bicarbonate. Compositions disclosed herein comprise amounts, concentrations, or ratios so as to avoid the formation of any significant precipitate disallowed by a drug approval agency, such as the U.S. Food and Drug Administration (FDA) or its foreign counterparts.

It would be understood that the concentrations or amounts of the sodium bicarbonate, calcium chloride, or other salt may be modified or adjusted in accordance with the solvent selected, as recognized in the art. For example, a preferred embodiment may contain a higher amount or concentration of calcium chloride in an aqueous/non-aqueous co-solvent.

Methods disclosed herein comprise the step of administering to a patient a sufficient or effective amount of the compositions disclosed herein at the site that has been administered a regional or local anesthesia. The composition can be administered at a site previously administered the anesthetic agent or can be administered concomitantly with the anesthetic agent.

In one embodiment, methods include administering compositions disclosed herein to an area of a patient, wherein the area has previously been administered or contains a regional or local anesthetic, and wherein the amount of the composition administered is sufficient to reverse a medically significant degree of numbness, yet provide the patient with control or relief of pain (chronic or acute) for a period of time, even in the absence of other pain relievers such as opioids or NSAIDs.

In another embodiment, methods include administering a regional or local anesthetic to the patient; and administering an inorganic or organic salt agent (e.g., bicarbonate) to an area of the patient that contains the regional or local anesthetic, and wherein the amount of inorganic or organic salt agent (e.g., bicarbonate) administered is sufficient to reverse the numbing effect of the anesthetic, yet still provide the patient with pain (chronic or acute) control or relief for a period of time. Thus, methods disclosed herein include providing anesthetic analgesia that does not induce a medically significant degree of numbness.

In an additional embodiment, methods include administering a regional or local anesthetic to the patient during a surgical or dental procedure, near completion of a surgical or dental procedure or immediately following a surgical or dental procedure; and administering an inorganic or organic salt agent (e.g., bicarbonate) into the area of the patient administered the regional or local anesthetic, wherein the amount of inorganic or organic salt agent (e.g., bicarbonate) administered is sufficient to provide the patient with pain (chronic or acute) control or relief without numbness for a period of time after the surgical or dental procedure.

Methods disclosed herein further include providing or extending pre- or post-operative pain (chronic or acute) control without the medically significant degree of numbness normally caused by administered local or regional anesthetic. Thus, for example, in various embodiments, compositions disclosed herein can be administered to a patient in need of control or relief of pain following reversal of numbing effect from an administered anesthetic agent.

The subject method therefore provides analgesia without a medically significant degree of numbness to a patient comprising the step of administering a buffer composition to an area of a mammalian, e.g., human, patient during, near completion of, or immediately following a surgical or dental procedure, wherein the area has previously been administered or contains a regional or local anesthetic agent, wherein the buffer composition comprises about 1% to about 15% bicarbonate, calcium, chloride, nitrate, phosphate, or sodium salt in aqueous solution, wherein the buffer composition is administered in an effective amount to reverse the medically significant degree of numbness in the patient without reversing the analgesic effect of the anesthetic agent, for at least 0.01 hours and up to about 72 hours after the surgical or dental procedure. For example, the subject method can be carried out using a 4.8% sodium bicarbonate salt in aqueous solution comprising about 1.1 mg/100 ml of a calcium salt, such as $CaCl_2$. The calcium salt solution can be made, for example, by adding about 1.11 mg $CaCl_2$ to 100 ml of solvent, wherein the preferred solvent is aqueous (e.g., water) containing 4.8% sodium bicarbonate.

In some embodiments, the pH of the buffer composition is in a range of from about 7 to about 9, in other embodiments, from about 7.4 to about 8.7, in still other embodiments, from about 7.6 to about 8.61.

Methods disclosed herein can include administration of the buffer composition multiple times following the medical or dental procedure.

In some embodiments, the method comprises administration of the buffer composition at a particular ratio to the dosage or amount of anesthetic agent. For example, in some embodiments, the buffer composition is administered at a ratio of at least about 0.4:1 to the anesthetic agent. In other embodiments, the buffer composition is administered at a ratio of 1:1, 2:1, 3:1, 4:1, 5:1, 6:1, 7:1, 8:1, 9:1 10:1 or greater to the anesthetic agent.

The method of the invention can be carried out at any site or area of the body where a local or regional anesthetic agent may be administered. Thus the methods disclosed herein can include administration of the anesthetic agent and/or the buffer composition topically, intradermally, intramuscularly, intravenously, subcutaneously, epidurally, by infusion or by injection, and can include administering to the torso, stomach, chest, head, scalp, neck, face, nose, ear, shoulder, back, arm, leg, thigh, ankle, knee, foot, toe, hand, wrist, finger, buttocks, groin, or a joint. The methods may alternatively be carried out in the area of the patient which has an incision or cut.

The methods disclosed herein can be carried out wherein the surgical or dental procedure comprises cancer or tumor surgery, trauma surgery, cosmetic surgery, abdominal surgery, head or neck surgery, orthopedic surgery, back or spine surgery, arthroscopic surgery, brain surgery, ear, nose or throat surgery, eye surgery, amputation, liposuction, rhinoplasty, graft or transplant surgery, a biopsy, skin surgery, breast surgery, prosthetic surgery, fetal surgery, gastroenterologic surgery, thoracic surgery, bladder surgery, heart surgery, liver surgery, pancreas surgery, kidney surgery, lung surgery, gallstone surgery, hernia surgery, shoulder, arm, leg, pelvis, hip, knee, elbow or ankle surgery, uterine or vaginal surgery, cesarean section or childbirth procedure or episiotomy, blood vessel surgery, prostate surgery, colon or rectal surgery, laser surgery, oral surgery, periodontal surgery, dental implant or tooth repair or extraction.

The buffer compositions for reversing a medically significant degree of numbness caused by administration of an anesthetic agent to a patient, without reversing analgesic effect of the anesthetic agent, may comprise a bicarbonate, nitrate, or phosphate salt in aqueous solution, and less than about 1.5 mg/100 ml calcium chloride.

Typically, the subject buffer composition is an aqueous solution comprising about 4.8% sodium bicarbonate and about 1.11 mg/100 ml calcium chloride. The composition may have a pH of greater than 7, or in some embodiments, be in a range of from about 7 to about 11, and in other embodiments from about 7 to about 9. In some embodiments compositions disclosed herein comprise a pH in a range of from about 7.6 to about 8.6.

Compositions disclosed herein which provide relief or control of pain (analgesia) from an administered local anesthetic agent without numbness (anesthetic effect), or LAAWON, can be an aqueous inorganic salt or organic buffer solution. An example of an effective LAAWON composition is about 4.8% sodium bicarbonate solution in water, and further comprising calcium salt, such as calcium chloride ($CaCl_2$), wherein the calcium salt is in an amount which does not cause a precipitate to form from or in the solution. The sodium bicarbonate can be substituted with other inorganic sodium, calcium, phosphate, or nitrate salts, as buffering or active agents, or with organic buffering or active agents, such as TRIS.

The term "inorganic salt or organic buffer agent," for purposes of the subject invention, refers to an agent, typically a salt which, in solution, is capable of being adjusted to a pH of about 7 or greater. A salt is typically an alkali or alkaline earth metal salt of an inorganic or organic acid, such as a salt of a weak acid, and strong base, or weak base. In order to achieve a pH of about 7 or greater, a salt is typically a salt of a weak acid and strong base, or of a salt of a weak acid and a weak base.

Typical cations of the salt are sodium, potassium, calcium, and magnesium. Typical anions are monovalent inorganic anions such as fluoride, bromide and chloride; multivalent organic anions such as carbonate, hydrogen carbonate; and multivalent inorganic anions such as sulphate, and phosphate.

Non-toxic inorganic anions of organic acids include anions of mono-like and dibasic organic acids such as acetate, chloride, gluconate, mono- or di-carboxylic acids, phosphate, and sulfate.

A LAAWON composition of the invention to be administered to a subject can be provided in a ratio of at least 0.4:1 (v/v) to the regional or local anesthetic, or greater, and are preferably administered at a ratio of about 1:1, 2:1, 3:1, 4:1, 5:1, 6:1, 7:1, 8:1, 9:1 10:1 ratio to the regional or local anesthetic administered. Typical amounts of the subject LAAWON composition administered is in at least a 1:1 ratio, and preferably a 2:1 ratio, to the regional or local anesthetic administered. Typical amounts of inorganic or organic salt agent salt (e.g., bicarbonate) administered are in solution at a concentration from about 1% to 15%, or preferably about 2 to 10%, or more preferably about 4 to 6%.

Typically, the buffer agent is present, depending upon solubility, in an amount of approximately 1M in aqueous solution. In the case of sodium bicarbonate, a 1 M, or meq/ml (84 mgs/ml) solution has a pH of about 7.6-8.6. Such a solution can be conveniently contained in a Dental dosage unit of a size of approximately 1.8 ml (typically about 2.2 mls in European practice) for application to the oral cavity, for example, as carried out in a conventional dental procedure.

Sufficient or effective amounts depend upon the desired effect, the anesthetic administered to the patient, the inorganic or organic salt agent administered that provides or extends pain control or relief to the patient, the location of administration and the form administered. Of course, as is typical for any treatment or therapy, different patients will exhibit different responses to treatment and some patients may not respond or respond inadequately to a particular treatment. Since every treated patient may not respond to a particular method, the methods set forth herein are not required to achieve pain control or relief without a medically significant degree of numbness in each and every patient, or a given population so treated. Accordingly, an amount sufficient or an amount effective means sufficiency or effectiveness in a particular patient, not a group of subjects or the general population.

It should be understood that the larger the dose and/or volume of local anesthetic used, the larger the dose and/or volume of the LAAWON composition should be used. Further, the closer in time the administration of LAAWON composition is to the administration of local or regional anesthetic agent, the more sedimentation of the base salt in the "depot" site, and the greater amount of analgesia (LAAWON) is provided.

A "sufficient" or "effective" amount, as used herein, means an amount that achieves or is likely to achieve a desired effect or outcome. Thus, in a method of the invention a sufficient or effective amount of a LAAWON composition will provide or extend pain control or relief without a medically significant degree of numbness in a given patient. In particular embodiments, pain control or relief provided to the patient without a medically significant degree of numbness provides, most preferably, a duration of effect for a range of about 0.1-72 hours, preferably at least about 0.01-12 hours, more preferably about 0.5-24 hours, even more preferably about 0.5-48 hours.

Without intending to limit embodiments disclosed herein, the mechanism of action for the composition is believed to result from a change of the anesthetic agent, e.g., lidocaine HCl, from the hydrochloride salt to its free base. This "molecular switch" from salt to free base is thus believed to provide for slower release of the anesthetic agent within the tissue, and transforming the effect from an anesthetic (inhibiting the nerve impulse) to an analgesic, affecting the opiate receptors or affecting the "afferent feeder" vessels to the nerve.

In one embodiment, an effective amount of bicarbonate-plus-calcium chloride is administered at a ratio of at least 0.4:1 of the anesthetic, and is typically administered at a ratio of 1:1 or greater (v/v), and preferably a ratio of 2:1 or greater. Thus, a bicarbonate solution of 1% to 15%, preferably about 4.8% to about 8.4% is administered at a volume ratio of 0.4:1 or greater to the volume of a 1-15% solution of anesthetic, preferably a 2-4% solution of anesthetic.

Administration of regional or local anesthetic, or a composition disclosed herein, include any mode (e.g., bolus dose or a slow or delayed release) or route of administration or delivery. Exemplary delivery and administration routes include oral (buccal, sublingual, alimentary, mucosal), intravenous, intra-arterial, intradermal, parenteral (e.g., subcutaneous, intramuscular), intra-tumor, intra-pleural, topical (dermal), transdermal, transmucosal, intra-cranial, intra-spinal, intra-tracheal, epidural, intra-ocular, intracavity, iontophoretic, rectal, vaginal, intrauterine, ophthalmic, optical (e.g., corneal), intraglandular, intraorgan, intralymphatic, intrapulmonary, intranasal and intrathecal.

Typically, an inorganic or organic salt agent will be administered in a fluid (e.g., aqueous or non-aqueous solution) having a pH equal to or greater than about pH 7, for example from about pH 7 to about 11 and more typically from about pH 7 to about 9 (e.g., from about 7.6 to about 8.6, such as with carbon dioxide). There is no upper limit to the pH of the composition useful for the subject invention except that, for practical purposes, a composition having a pH of less than about 11 is understood to be more compatible with mammalian tissue. Skin sensitivity to basic substances is such that a pH typically not greater than 10 and more typically not greater than 9 is used. In practice, an upper limit of pH is determined by the nature of the salt, any buffer or base present, and the concentration of inorganic or organic salt agent.

A desired pH can be maintained in a buffer using carbon dioxide or calcium chloride. For example, a buffer can maintain a pH of about 7 or more, or a pH of at least 7.5, or a pH from about 7.6 to 8.6. Typical buffers include inorganic and organic buffers including phosphate, citrate, bicarbonate and the like. The upper limit of the pH is not limited except that, the upper limit of the pH can be affected by the nature of the salt, and any buffer, and concentration of base that may be used to adjust the pH. A desired pH can be obtained using carbon dioxide, for example.

A regional or local anesthetic, or inorganic or organic salt agent, can be administered in a non-toxic pyrogen-free, fluid mixture. The term "non-toxic" used herein means not causing death of a patient or undesirable side effects, such as permanent damage to a nerve or muscle. Systemic toxicity of agents and anesthetics administered in accordance with various embodiments are optionally low.

The term "pyrogen-free" when applied to regional or local anesthetic, or inorganic or organic salt agent suitable for administration to a patient means that the anesthetics and agents do not contain substances known to cause a pyrogenic response. Pyrogens can be removed from mixtures by methods known to one skilled in the art.

Administration of regional or local anesthetic or inorganic or organic salt agent disclosed herein can be performed during a surgical or dental procedure, or within a specified period of time prior to or after a surgical or dental procedure (e.g., within 72, 48, 24, 12, 6, 2, or 1 hours, or less than one hour, such as within 1, 5, 15, 30 minutes, or even simultaneously).

Administration of regional or local anesthetic or inorganic or organic salt agent disclosed herein can also be performed multiple times (e.g., 1-10, 1-5 or 1-3 times) per minute, hour, day, week or month. For example, in various embodiments, an inorganic or organic salt agent is administered to a patient immediately following administration of regional or local anesthetic. In various additional embodiments of the methods of the invention, an inorganic or organic salt agent is administered to a patient within about 1-5, 1-10, 2-10, 5-20, 15-30, 30-60 or 60-120 minutes after administration of regional or local anesthetic.

The method can optionally be used in conjunction with a vasoconstrictor to prolong the duration of the action. For example, an anesthetic can be administered concomitantly with a vasoconstrictor. The term "vasoconstrictor" used here means an agent capable of causing constriction of blood vessels including various sympathomimetic drugs such as epinephrine, norepinephrine, levonordenphedrine and dopamine. Typically, epinephrine is administered in a dilution of 1:100,000 mixed with a solution of lidocaine and supplied in 1.8 ml capsules.

The methods disclosed herein are appropriate in any surgical or dental procedure or context in which a local or regional anesthetic is used or has already been administered to a patient. Non-limiting examples of surgical and dental procedures include cancer or tumor surgery, trauma surgery, cosmetic surgery, abdominal surgery, head or neck surgery, orthopedic surgery, back or spine surgery, arthroscopic surgery, brain surgery, ear, nose or throat surgery, eye surgery, amputation, liposuction, rhinoplasty, graft or transplant surgery, a biopsy, skin surgery, breast surgery, prosthetic surgery, fetal surgery, gastroenterologic surgery, thoracic surgery, bladder surgery, heart surgery, liver surgery, pancreas surgery, kidney surgery, lung surgery, gallstone surgery, hernia surgery, shoulder, arm, leg, pelvis, hip, knee, elbow or ankle surgery, uterine or vaginal surgery, blood vessel surgery, prostate surgery, colon or rectal surgery, laser surgery, routine dentistry, oral surgery, periodontal surgery, dental implant or tooth repair or extraction. Additional non-limiting examples of surgical procedures include child birth (e.g., natural vaginal birth, in which labor is not induced or labor is induced) and child birth related surgery, such as surgery during childbirth, including cesarean section, episiotomy, etc., and surgery following childbirth, such as labioplasty, stomach tightening, breast augmentation or enlargement, varicose vein treatment, etc.

The methods disclosed herein can employ pharmaceutical compositions and formulations. As used herein the terms "pharmaceutically acceptable" and "physiologically acceptable" mean a biologically compatible formulation, gaseous, liquid or solid, or mixture thereof, which is suitable for one or more routes of administration, in vivo delivery or contact. A formulation is compatible in that it does not destroy activity of an active ingredient therein, or induce adverse side effects that far outweigh any therapeutic benefit or effect.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents.

Co-solvents may be added. Non-limiting examples of co-solvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary active compounds (e.g., preservatives, antioxidants, antimicrobial agents including biocides and biostats such as antibacterial, antiviral and antifungal agents) can also be incorporated. Preservatives and other additives include, for example, antimicrobials, anti-oxidants, chelating agents and inert gases (e.g., nitrogen).

Preservatives include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins. Antimicrobials include, antibacterial, antiviral, antifungal and antiparasitics that kill or destroy (-cidal) or inhibit (-static) contamination by or growth, infectivity, replication, proliferation, reproduction of the microbial organism.

Pharmaceutical compositions can optionally be formulated to be compatible with a particular route of administration. Thus, pharmaceutical compositions include carriers (excipients, diluents, vehicles or filling agents) suitable for administration by various routes and delivery, regionally, locally or systemically, ex vivo or in vivo, as set forth herein or known to the skilled artisan.

Formulations suitable for parenteral administration include aqueous and non-aqueous solutions, suspensions or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable or synthetic oils. Examples of non-aqueous solvents are propylene glycol, polyethylene glycol, vegetable oils such as olive oil, cotton seed or sesame seed, oror oil suspensions, and injectable organic esters such as ethyl oleate. Intravenous vehicles include fluid and nutrient replenishers, electrolyte replenishers (such as those based on Ringer's dextrose).

For transmucosal or transdermal administration (e.g., topical contact), penetrants can be included in the pharmaceutical composition. Penetrants include, for example, for transmucosal administration, detergents, bile salts, and fusidic acid derivatives. For transdermal administration, the active ingredient can be formulated into aerosols, sprays, ointments, salves, gels, pastes, lotions, oils or creams.

For oral administration, pharmaceutical compositions include capsules, cachets, lozenges, tablets or troches, as powder or granules. Oral administration formulations also include a solution or a suspension (e.g., aqueous liquid or a non-aqueous liquid; or as an oil-in-water liquid emulsion or a water-in-oil emulsion).

For topical administration, for example, to skin, pharmaceutical compositions typically include ointments, creams, lotions, pastes, gels, sprays, aerosols or oils. Carriers which may be used include Vaseline, lanolin, polyethylene glycols, alcohols, transdermal enhancers, and combinations thereof.

Additional pharmaceutical formulations appropriate for administration are known in the art (see, e.g., Gennaro (ed.), Remington: The Science and Practice of Pharmacy, 20.sup.th ed., Lippincott, Williams & Wilkins (2000); Ansel et al., Pharmaceutical Dosage Forms and Drug Delivery Systems, 7th ed., Lippincott Williams & Wilkins Publishers (1999); Kibbe (ed.), Handbook of Pharmaceutical Excipients American Pharmaceutical Association, 3.sup.rd ed. (2000); and Remington's Pharmaceutical Principles of Solid Dosage Forms, Technonic Publishing Co., Inc., Lancaster, Pa., (1993)).

The term "patient" or "subject" are used interchangeably herein and refer to animals, typically mammals, such as humans, non-human primates (gorilla, chimpanzee, orangutan, macaque, gibbon), domestic animals (dog and cat), farm and ranch animals (horse, cow, steer, goat, sheep, goat, pig), marine mammals such as porpoises, whales, killer whales (orcas), and the like, laboratory and experimental animals (mouse, rat, rabbit, guinea pig). Human subjects include children, for example, newborns, infants, toddlers and teens, from the ages of 1 and 5, 5 and 10 and 10 and 18 years, adults from the ages of 18 and 60 years, and the elderly, for example, from the ages of 60 and 65, 65 and 70 and 70 and 100 years.

Patients and subjects include mammals (e.g., humans) in need of treatment, that is, for example, they are at risk of or are experiencing undesirable pain. Such patients and subjects therefore include those that are undergoing a surgical or dental procedure that results or is likely to result in ("at risk of") pain due to the surgical or dental procedure.

Patients and subjects can therefore be treated in order to inhibit or reduce the likelihood or risk of developing pain. The result of such treatment can be to provide or extend pain control to the patient or subject.

Embodiments disclosed herein further provide kits, including regional and local anesthetics, and inorganic or organic salt agents, and pharmaceutical formulations thereof, packaged into suitable packaging material, optionally in combination with instructions for using the kit components, e.g., instructions for providing or extending pain control or relief. Invention kits can include therein an individual container or in a mixture and all of the various containers can be within single or multiple packages that comprise the kit. A delivery device, such as a syringe, applicator, transdermal patch, or the like, can also be included in a kit in accordance to the subject invention.

One embodiment of a kit can further include a pH-sensor to confirm the pH of the solution prior to its administration. For example, a pH indicator can be included as a pH-sensor component of the kit, or can be manufactured as part of, or integral with, the packaging. Indicators for pH determination are well known in the art, and can be electronic (measuring differences in electrolytes across a semipermeable membrane), or can be a substrate, e.g., a paper strip, infused with a pH-sensitive dye, such as litmus or Nitrazepam. As an example, a litmus strip, or portion thereof, can be made or provided integral with the packaging of the kit whereby, prior to administration or the LAAWON agent, a drop of the LAAWON agent is absorbed or "spotted" onto the litmus/Nitrazepam strip, and pH is determined by the color of the spot on the litmus strip. The pH-sensor can be qualitative or quantitative, and preferably provides a pH determination within a specified range useful for its intended use. For the subject invention, a qualitative pH sensor can confirm a pH range between about 7 and about 9, preferably between about 7.6-8.6.

A kit in accordance with various embodiments therefore can include in a packaging, a local/regional anesthetic agent, a LAAWON composition, syringes/needles for administration of the anesthetic agent and/or the LAAWON composition, sterile drapes, towels, or the like to carry out the procedure.

The term "packaging material" refers to a physical structure housing the components of the kit. The packaging material can preferably maintain the components in sterile condition for a desired amount of time, and can be made of material commonly used for such purposes (e.g., paper, corrugated fiber, glass, plastic, foil, ampules, etc.).

The label or package insert can further include appropriate written instructions. Thus, in various embodiments, a kit includes a label or package insert including instructions for practicing a method of the invention.

Instructions may additionally include indications of a satisfactory clinical endpoint or any adverse symptoms or complications that may occur. Instructions may further include storage information, expiration date, or any information required by regulatory agencies such as the Food and Drug Administration for use in a human subject.

The instructions may be on "printed matter," e.g., on paper or cardboard within the kit, on a label affixed to the kit or packaging material, or attached to a vial or tube containing a component of the kit. Instructions may comprise audio or video medium and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to "an anesthetic" includes a plurality of anesthetics and reference to "an inorganic or organic salt agent" can include multiple inorganic or organic salt agents, and so forth.

As used herein, reference to a numerical value or numerical range includes reference to a fraction of such values, and whole integers and fractions within or encompassing such ranges of the values or integers within or encompassing ranges unless the context clearly indicates otherwise. Thus, for example, reference to a numerical value of 7 includes reference to 7.1, 7.2, and so forth. Reference to a range of 1-15%, includes 2, 3, 4, 5, 6, 7, 8%, etc., as well as 1.1, 1.2, 1.3, 1.4, 1.5%, etc., 2.1, 2.2, 2.3, 2.4, 2.5%, etc., and so forth. In another example, reference to a unit of time, such as within 72 hours, means within 71, 70, 69, 68 . . . 1 hour, or minutes, e.g., 59, 58, 57, 56, 55 . . . 1 minute, and so forth. In yet another example, reference to a ratio of 2:1 includes 2:1.1, 2:1.2, 2:1.3, 2:1.4, 2.1:1, 2.2:1, 2.3:1, 2.4:1, and so forth.

The invention is generally disclosed herein using affirmative language to describe the numerous embodiments. The invention also specifically includes embodiments in which particular subject matter is excluded, in full or in part, such as substances (e.g., particular anesthetics or inorganic or organic salt agents) or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments have been described. Nevertheless, it will be understood that various modifications may be made without departing from the spirit and scope of the invention. Accordingly, the following examples are intended to illustrate but not limit the scope of invention described in the claims.

EXAMPLE

Experimental results employing a method and composition disclosed herein were obtained from a study conducted on a 61 year-old consenting male in good health. The results show that a local anesthetic which typically provides an anesthetic or numbing effect can be selectively reversed to provide an analgesic (control or relief of pain) without numbness, or LAAWON. The variables tested demonstrate the amount of the subject composition required for LAAWON, the time required to induce the onset of LAAWON, the duration of LAAWON, and investigate potential side effects from the composition or method of the invention.

The results demonstrate that LAAWON can be successfully induced with all of the anesthetic agents tested. With most of the tested agents, the duration of LAAWON was relatively brief. Lidocaine, however, produced a notably long period of 191 minutes of LAAWON with an aqueous buffer composition of sodium bicarbonate. This long period of LAAWON was very significantly extended to 283 minutes, and the time to induce LAAWON was substantially reduced, by the use the aqueous buffer composition of both sodium bicarbonate and calcium chloride that is the subject of the present invention.

Materials and Methods.

Four different anesthetic agents were used:

2% Lidocaine HCl with 1:100,000 epinephrine—supplied in a 1.8 ml dental cartridge manufactured for Carestream Health, Inc., by Cooke-Waite, Novocol Pharmaceuticals of Canada Inc., Cambridge, Ontario Canada, N1R 6X3;

2% CARBOCAINE HCl with 1:20,000 levonordenphedrine—supplied in a 1.8 ml dental cartridge (ISOCAINE) manufactured by Novocol Pharmaceuticals of Canada, Inc., Cambridge, Ontario, Canada, N1R 6X3;

3% CARBOCAINE HCl Plain—supplied in a 1.8 ml dental cartridge, manufactured for Cooke-Waite by Carestream Health, Inc., by Novocol Pharmaceutical of Canada Inc., Cambridge, Ontario, Canada, N1R 6X3; and 0.5% Bupivacaine HCl with 1:200,000 epinephrine—supplied in a 1.8 ml dental cartridge (MARCAINE) manufactured for Carestream Health, Inc., by Novocol Pharmaceutical of Canada Inc., Cambridge, Ontario, Canada, N1R 6X3.

The hairless bare forearms of our consenting volunteer were used as our test sites. The bicep areas were used for the controls. All the sites were separated by at least 2 inches to prevent contamination of results from one test site to the other test site. All test sites were cleaned with alcohol swabs prior to needle placement and all sites were observed for untoward reactions, excessive bleeding, ulceration or necrosis. Observation continued for three days after testing was completed.

The same amounts of each local anesthetic agent (0.9 mls) were used in all tests. Injections of local anesthetic were made using a dental syringe, stainless steel, sterile—manufacturer 100-9808, Henry Schein of Melville, N.Y. Dental needle, stainless steel, sterile 1" 29 gauge manufacturer 2015-09-MF4-17044—Septoject.

In the case of the controls, after the injection of anesthetic into a control site, no further injections were made to that control site. The time of each anesthetic injection was recorded, as was the time at which the full return of sensation to pin prick (Medipin™) was experienced. The full return of sensation was confirmed by testing with heat (spoon handle @ 100 F), cold (ice cube), pressure using a pencil eraser and digital pressure, and pain using a 21 gauge 1½-inch sterile graduating syringe pushed into the site 10 mm and moved up and down in the tissue. In the TABLE below, for controls, the column titled "Total Duration of any Anesthetic and/or Analgesic Effect" presents the total duration, in minutes, between the injection of anesthetic into a control site and the time at which full sensation returned to the control site.

In the case where LAAWON was induced through the use of aqueous buffer compositions, each LAAWON site, once numbed by the injection of anesthetic, was injected with either 2 mls of 4.8% of sterile sodium bicarbonate (pH 7.8 to 8.6) or 2 mls of sodium bicarbonate with 1.1 mgs/100 mls of Calcium Chloride (pH 7.8-8.6). Sodium Bicarbonate 4.8% buffered, (pH 7.8-8.6) was supplied sterile and refrigerated in a 10 ml vial by Compounding Docs, Inc., 5499 N. Federal Highway, Unit G, Boca Raton, Fla. 33487. The 4.8% Sodium Bicarbonate (pH 7.8-8.6) with 0.1 mM, or about 1.1 mgs/100 ml Calcium Chloride sterile and refrigerated was provided by Compounding Docs, Inc., 5499 N. Federal Highway, Unit G, Boca Raton, Fla. 33487. The LAAWON composition was administered using an i.m./subcutaneous—sterile latex free syringe 3 ml (manufacturer Belton Dickinson & Co., FranklinLakes, N.J. 07417) using a 27-gauge Luerlock™ needle) 27 G 1.1½" Luerlock™ manufacturer Tyco/Helathco Kendall monoject needle sterile ref. 11888-27112.

The LAAWON aqueous buffer composition was administered twenty to thirty minutes after the initial anesthetic injection, with the times of administration recorded, by a second injection of either buffered 4.8% sodium bicarbonate buffered (pH7.8-8.6) or 4.8% sodium bicarbonate with about 1.1 mg/100 ml calcium chloride. Each test site was separated by 2 inches to prevent contamination. The choice of local anesthetic was recorded for each test. The second LAAWON-inducing injection was blinded and given a number according to the site to be used. Return of sensation was determined by pinprick (Medipin™), and confirmed by testing with heat (spoon handle @ 100° F.), cold (ice cube), and pressure using a pencil eraser and digital pressure. Once sensation returned to the site, the duration of local anesthesia analgesia without numbness (LAAWON) was determined using a 21 gauge 1½-inch sterile graduating syringe pushed into the site 10 mm and moved up and down in the tissue to test for pain. The subject was considered to be in the LAAWON state for the period during which he experience sensation from pin prick, hot, cold, and pressure, but did not experience pain from the 21 gauge syringe. When the subject did report feeling pain from the 21 gauge syringe, the period of LAAWON was considered to be ended.

In the TABLE below, where a LAAWON agent is injected, the column titled "Total Duration of any Anesthetic and/or Analgesic Effect" presents the total duration, in minutes, between the injection of anesthetic into a LAAWON site and the time at which full sensation, i.e. sensation of pinprick, hot, cold, pressure, and pain, returned to the LAAWON site. The column titled "Time to Initiate LAAWON" presents the total duration, in minutes, of the period between the time at which the LAAWON agent was injected into the pre-anesthetized LAAWON site and the time at which LAAWON began to be experienced, i.e., sensation of pinprick, hot, cold, and pressure, but not pain. The column titled "Duration of LAAWON" presents the total duration, in minutes, of the period between the time at which LAAWON began to be experienced and the time at which full sensation returned, i.e., sensation of pinprick, hot, cold, pressure, and pain.

The results of the testing are shown in the TABLE, below:

TABLE

| Local Anesthetic | LAAWON Agent | Total Duration of any Anesthetic and/or Analgesic Effect | Time to Initiate LAAWON | Duration of LAAWON |
|---|---|---|---|---|
| 0.9 ml Lidocaine, 2% w/epinephrine 1:100,000 (Control) | No LAAWON agent | 484 mins | N/A | N/A |

| Local Anesthetic | LAAWON Agent | Total Duration of any Anesthetic and/or Analgesic Effect | Time to Initiate LAAWON | Duration of LAAWON |
|---|---|---|---|---|
| 0.9 ml Lidocaine, 2% w/epinephrine 1:100,000 | 2 ml, 4.8% Sodium Bicarb | 330 mins | 118 mins | 191 mins |
| 0.9 ml Lidocaine, 2% w/epinephrine 1:100,000 | 2 ml, 4.8% Sodium Bicarb/1.1 mg/100 ml $CaCl_2$ | 399 mins | 94 mins | 283 mins |
| 0.9 ml CARBOCAINE, 2% w/levonordenphedrine (Control) | No LAAWON agent | 394 mins | N/A | N/A |
| 0.9 ml CARBOCAINE, 2% w/levonordenphedrine 1:20,000 | 2 ml, 4.8% Sodium Bicarb | 102 mins | 55 mins | 25 mins |
| 0.9 ml CARBOCAINE, 2% w/levonordenphedrine 1:20,000 | 2 ml, 4.8% Sodium Bicarb/1.1 mg/100 ml $CaCl_2$ | 104 mins | 48 mins | 35 mins |
| 0.9 ml CARBOCAINE, 3% (Control) | No LAAWON agent | 115 mins | N/A | N/A |
| 0.9 ml CARBOCAINE, 3% | 2 ml, 4.8% Sodium Bicarb | 109 mins | 66 mins | 23 mins |
| 0.9 ml CARBOCAINE, 3% | 2 ml, 4.8% Sodium Bicarb/1.1 mg/100 ml $CaCl_2$ | 116 mins | 56 mins | 35 mins |
| 0.9 ml MARCAINE, 0.5% w/epinephrine 1:200,000 (Control) | No LAAWON agent | 581 mins | N/A | N/A |
| 0.9 ml MARCAINE, 0.5% w/epinephrine 1:200,000 | 2 ml, 4.8% Sodium Bicarb | 400 mins | 372 mins | 11 mins |
| 0.9 ml MARCAINE, 0.5% w/epinephrine 1:200,000 | 2 ml, 4.8% Sodium Bicarb/1.1 mg/100 ml $CaCl_2$ | 463 mins | 445 mins | 9 mins |

This study demonstrated that adding 1.1 mg/100 ml of CaCl2, to 4.8% sodium bicarbonate solution, in certain instances, decreased the time to induce LAAWON, and increased the duration of LAAWON compared to induction of LAAWON using a 4.8% sodium bicarbonate solution alone (without calcium chloride). Specifically, the administration of a composition disclosed herein (4.8% sodium bicarbonate and 1.1 mgs/100 ml $CaCl_2$) decreased the time to induce LAAWON, involving 2% Lidocaine with 1:100,000 epinephrine, by 24 minutes and increased the duration LAAWON from 3 hours 11 minutes to 4 hours 43 minutes compared to a 4.8% sodium bicarbonate solution alone (without calcium chloride). The subject composition and method also shortened LAAWON induction times for Carbocaine 3% Plain by 10 minutes (from 66 minutes to 56 minutes) and extended the duration of LAAWON by 12 minutes compared to a 4.8% sodium bicarbonate solution alone (without calcium chloride). The Carbocaine 2% with 1:20,000 levonordenphedrine time to induce LAAWON was decreased (from 55 minutes to 48 minutes) by 7 minutes and the duration of LAAWON increased by 10 minutes (from 25 to 35 minutes) compared to a 4.8% sodium bicarbonate solution alone (without calcium chloride).

MARCAINE 0.5% was less responsive to calcium chloride, taking 7 hours 25 minutes to induce the onset of LAAWON (with the combination solution of sodium bicarbonate and calcium chloride) versus 6 hours 12 minutes to induce the onset of LAAWON with 4.8% sodium bicarbonate alone (without calcium chloride). The duration of LAAWON was reduced from 11 minutes with 4.8% sodium bicarbonate alone (without calcium chloride) to 9 minutes using the 4.8% sodium bicarbonate and 1.1 mg/100 ml calcium chloride composition (the LAAWON composition) of the invention.

The study demonstrates that adding 1.1 mg/100 ml of calcium chloride to the sodium bicarbonate aqueous buffer solution to form the LAAWON composition of the invention improves the speed of induction and duration of LAAWON of amide local anesthetics, especially with Lidocaine 2% with epinephrine, where the induction process was shortened by 24 minutes and LAAWON was extended from 3 hours 11 minutes to 4 hours 43 minutes.

The invention claimed is:

1. A method for reducing onset time and extending duration of analgesia effect without numbness effect experienced by a patient administered a local or regional anesthetic selected from lidocaine, Articaine, Bupivacaine, and mepivacaine to induce a numbing effect in an area of a body of a patient, said method comprising:
in the area of the body of the patient previously administered the local or regional anesthetic, administering a solution containing greater than zero, but less than about 1.5 mg per 100 ml of calcium chloride salt and 3% to 10% sodium bicarbonate salt to create analgesia effect but without numbness effect in the area of the body of said patient administered or containing the local or regional anesthetic.

2. The method of claim 1, wherein said sodium bicarbonate solution is a 4.8% sodium bicarbonate solution.

3. The method of claim 1, wherein said composition comprises about 0.10 mg to about 1.2 mg calcium chloride per 100 ml of said composition.

4. The method of claim 1 wherein the volume of the composition administered is about 1-15 ml.

5. The method of claim 1, wherein the calcium chloride and sodium bicarbonate salt solution is administered prior to a loss of numbing effect from the administration of the local or regional anesthetic.

6. The method of claim 1, wherein the area of the body of the patient is an incision or cut.

7. The method of claim 1, wherein the calcium chloride and sodium bicarbonate salt solution is administered multiple times.

8. The method of claim 1, wherein the regional or local anesthetic is administered topically, intradermally, intramuscularly, intravenously, subcutaneously, epidurally, by infusion, or by injection.

9. The method of claim 1, wherein a ratio of the amount of the calcium chloride and sodium bicarbonate salt solution administered to the amount of the regional or local anesthetic composition administered is at least about 0.4:1 (v/v).

10. The method of claim 9, wherein a ratio of the amount of the calcium chloride and sodium bicarbonate salt solution administered to the amount of regional or local anesthetic administered is about 1:1, 2:1, 3:1, 4:1, 5:1, 6:1, 7:1, 8:1, 9:1, or 10:1 (v/v).

11. The method of claim 1, wherein the calcium chloride and sodium bicarbonate salt solution has a pH range from about 7.0 to about 11.0.

12. The method of claim 1, wherein the calcium chloride and sodium bicarbonate salt solution is administered in a surgical or dental procedure, said procedure being selected from the group consisting of:

cancer or tumor surgery, trauma surgery, cosmetic surgery, abdominal surgery, head or neck surgery, orthopedic surgery, back or spine surgery, arthroscopic surgery, brain surgery, ear, nose or throat surgery, eye surgery, amputation, liposuction, rhinoplasty, graft or transplant surgery, a biopsy, skin surgery, breast surgery, prosthetic surgery, fetal surgery, gastroenterologic surgery, thoracic surgery, bladder surgery, heart surgery, liver surgery, pancreas surgery, kidney surgery, lung surgery, gallstone surgery, hernia surgery, shoulder, arm, leg, pelvis, hip, knee, elbow or ankle surgery, uterine or routine child birth with epidural, vaginal surgery, cesarean section procedure or episiotomy, blood vessel surgery, prostate surgery, colon or rectal surgery, laser surgery, routine dental procedure, oral surgery, periodontal surgery, dental implant and tooth repair or extraction.

13. The method of claim 1 wherein said composition is a 4.8% sodium bicarbonate salt solution further comprising about 1.11 mg calcium chloride per 100 ml of said composition.

14. A method of reversing a medically significant numbing effect of lidocaine or mepivacaine administered to an area of a body of a patient as a local or regional anesthetic agent, without reversing pain-relief or pain control effect of the anesthetic agent administered to the patient, said method comprising:

administering to the patient, in the area of the body of the patient administered or containing the local or regional anesthetic, an effective amount of a calcium chloride and sodium bicarbonate salt solution containing greater than zero, but less than about 1.5 mg per 100 ml of calcium chloride salt and 3% to 10% sodium bicarbonate salt;

wherein the time to initiation of the analgesia without numbness is decreased, and the duration of analgesia without numbness is increased, compared with the time of initiation and duration of analgesia without numbness when a 1% to 15% bicarbonate salt solution without calcium salt is administered.

* * * * *